US008685417B2

(12) United States Patent
Schmidt et al.

(10) Patent No.: US 8,685,417 B2
(45) Date of Patent: Apr. 1, 2014

(54) POLYMER ENCAPSULATION AND/OR BINDING

(75) Inventors: Scott C. Schmidt, West Chester, PA (US); Michael S. Mendolia, Philadelphia, PA (US); Peter A. Callais, Conroe, TX (US)

(73) Assignee: Arkema, Inc., King of Prussia, PA (US)

( * ) Notice: Subject to any disclaimer, the term of this patent is extended or adjusted under 35 U.S.C. 154(b) by 448 days.

(21) Appl. No.: 12/519,292

(22) PCT Filed: Dec. 12, 2007

(86) PCT No.: PCT/US2007/087144
§ 371 (c)(1),
(2), (4) Date: Jun. 15, 2009

(87) PCT Pub. No.: WO2008/079677
PCT Pub. Date: Jul. 3, 2008

(65) Prior Publication Data
US 2010/0010103 A1    Jan. 14, 2010

Related U.S. Application Data

(60) Provisional application No. 60/875,961, filed on Dec. 20, 2006.

(51) Int. Cl.
*A61K 9/00* (2006.01)
(52) U.S. Cl.
USPC .......................................................... 424/400
(58) Field of Classification Search
USPC .......................................................... 424/400
See application file for complete search history.

(56) References Cited

U.S. PATENT DOCUMENTS

| | | | |
|---|---|---|---|
| 5,281,698 A | 1/1994 | Nitecki | |
| 5,446,090 A | 8/1995 | Harris | |
| 5,643,575 A | 7/1997 | Martinez et al. | |
| 5,932,462 A | 8/1999 | Harris et al. | |
| 5,939,453 A | 8/1999 | Heller et al. | |
| 6,224,793 B1 * | 5/2001 | Hoffman et al. | 264/4.1 |
| 6,255,448 B1 | 7/2001 | Grimaldi et al. | |
| 6,465,002 B1 * | 10/2002 | Mathiowitz et al. | 424/426 |
| 6,552,170 B1 | 4/2003 | Thompson et al. | |
| 6,569,967 B1 | 5/2003 | Couturier et al. | |
| 6,610,802 B2 | 8/2003 | Roos et al. | |
| 6,638,994 B2 | 10/2003 | Crooks et al. | |
| 6,646,079 B2 | 11/2003 | Guerret et al. | |
| 6,692,914 B1 * | 2/2004 | Klaerner et al. | 435/6.11 |
| 6,803,438 B1 | 10/2004 | Brocchini et al. | |
| 6,828,025 B2 | 12/2004 | Ali et al. | |
| 6,841,641 B2 * | 1/2005 | Olson et al. | 526/328.5 |
| 6,890,522 B2 | 5/2005 | Frechet et al. | |
| 6,939,564 B2 * | 9/2005 | Ranger et al. | 424/497 |
| 7,094,810 B2 | 8/2006 | Sant et al. | |
| 7,214,810 B2 | 5/2007 | Couturier et al. | |
| 2004/0010060 A1 | 1/2004 | Joanicot et al. | |
| 2004/0077873 A1 | 4/2004 | Guerret et al. | |
| 2004/0143035 A1 | 7/2004 | Goebelt et al. | |
| 2005/0065119 A1 | 3/2005 | Couturier et al. | |
| 2005/0180922 A1 | 8/2005 | Discher et al. | |
| 2006/0142506 A1 * | 6/2006 | Breitenkamp et al. | 525/482 |
| 2007/0078513 A1 | 4/2007 | Campbell | |
| 2007/0160561 A1 | 7/2007 | Ouali et al. | |
| 2007/0180561 A1 | 8/2007 | Eby | |
| 2008/0300348 A1 | 12/2008 | Haddleton et al. | |
| 2009/0220614 A1 | 9/2009 | Qin et al. | |
| 2009/0221739 A1 | 9/2009 | Knischka et al. | |

FOREIGN PATENT DOCUMENTS

WO    WO 2006/003352    1/2006

OTHER PUBLICATIONS

Becker et al. Chem. Commun., 2003, 180-181.*
Breitenkamp et al. Macromolecules 2002, 35, 9249-9252.*
Moon and Kang. Macromolecular Research, vol. 13, No. 3, pp. 229-235 (2005).*
Dettmer et al. Macromolecules 2004, 37, 5504-5512.*
Lutz and Laschewsky. Macromol. Chem. Phys. 2005, 206, 813-817.*
Goto, A. et al., Kinetic Studt on Nitroxide-Mediated Free Radical Polymerizationo of tert-Butyl Acrylate, Macromolecules, 1999, 32, 618-623.
Hawker, C. et al., Initiating Systems for Nitroxide-Mediated "Living" Free Radical Plymerizations: Synthesis and Evaluation, Macromolecules, 1996, vol. 29, No. 16, 5245-5254.
Benoit, D. et al., Controlled Free-Radical Polymerization in the Presence of a Novel Asymmetric Nitroxyl Radical, Poly. Prepr. 1997, 38(1), 729-730.
Hawker, C. et al., Development of a Universal Alkoxyamine for Living Free Radical Polymerizations Using Combinatoral Techniques, Polym. PMater. Sci. Eng. 1999, 80, 90-91.
Guillaneuf, Yohann, et al., "Nitroxide-Mediated Polymerization of Methyl Methacrylate Using an SG1-Based Alkoxyamine: How the Penultimate Effect Could Lead to Uncontrolled and Unliving Polymerization", Macromol. Chem. Phys., 2006, 207, 1278-1288.

* cited by examiner

*Primary Examiner* — David J Blanchard
*Assistant Examiner* — Devang Thakor
(74) *Attorney, Agent, or Firm* — Thomas F. Roland

(57) ABSTRACT

Encapsulation of and binding to pegylated bioactive molecules via functionalized comb, block, branched type polymers formed by nitroxide mediated controlled radical polymerization is disclosed.

21 Claims, No Drawings

POLYMER ENCAPSULATION AND/OR BINDING

FIELD OF THE INVENTION

This invention relates to functionalized and/or tailored polymers and in particular to encapsulation of and binding to materials or functional agents via functionalized and/or tailored homopolymers, copolymers, branched polymers and block copolymers, formed by nitroxide mediated controlled radical polymerization.

BACKGROUND OF THE INVENTION

The modification of materials with groups derived from polyethylene glycol (PEG) is known as PEGylation. PEGylation is now widely used for the modification of bioactive molecules, such as proteins, peptides, antibody fragments, oligonucleotides, and the like for, use as drugs.

Although bioactive molecules such as protein and peptide drugs hold great promise as therapeutic agents, many are degraded by proteolytic enzymes, can be rapidly cleared by the kidneys, generate neutralizing antibodies, have a short shelf life, have low solubility, and/or have a short circulating half-life. PEGylation of these materials can overcome these and other shortcomings. The ability of PEGylation to decrease clearance typically is not a function of the number of PEG groups attached to the protein, but is related to the overall molecular weight of the altered proteins. By increasing the molecular mass of proteins and peptides and shielding them from proteolytic enzymes, PEGylation improves pharmacokinetics. Among the other advantages of PEGylation are: increased water solubility, increased bioavailability, increased blood circulation, decreased protein aggregation, decreased immunogenicity, reduced toxicity, and decreased frequency of administration.

Branched polymers can provide a single non-linear polymer molecule with a high overall molecular weight. Branched or star-shaped polymers comprising a plurality of polymer arms attached to a central core and having a single reactive group for conjugation to a biologically active molecule have been described, for example, in U.S. Pat. Nos. 5,643,575, and 5,932,462, the disclosures of which are both incorporated herein by reference. Although these branched polymers are useful for attaching a high molecular weight polymer to a molecule at a single attachment site without using an extremely long polymer chain, the methods for forming the branched PEG molecules are difficult and require extensive purification of the PEG polymers prior to attachment to the core molecule as well as purification/removal of partially PEGylated polymer intermediates following attachment.

WO 2006/003352, the disclosure of which is incorporated herein by reference, describes the use of atom transfer polymerization (ATRP) and reversible addition fragmentation transfer (RAFT) in the preparation of comb polymers from monomers that contain alkoxy polyethers. The disclosure describes many shortcomings of the prior art and benefits of using a controlled polymerization process, however, ATRP polymerizations also have several drawbacks including, but not limited to, slow polymerization kinetics, residual metallic byproducts, scale-up difficulties, and limited polymer composition and molecular weight ranges. The metallic by-products can be detrimental in biological systems and require removal, which is difficult and requires laborious procedures. U.S. Pat. No. 6,610,802, for example, describes these byproducts and discloses the disadvantage of ATRP processes. Furthermore, the large amount of metallic control agent required can cause discoloration as well as corrosion issues in some reactors. Sensitivity to oxygen and to certain functional groups, such as acids, is an additional limitation encountered with this technique as it leads to poor control and impurities.

RAFT uses dithio esters of carbamates, xanthates, and trithiocarbonates, such as dibenzyl trithiocaronate (DBTTC) as radical control agents. However, for the RAFT process to function effectively, the RAFT agent must be carefully chosen based on the type of monomer used and the polymerization rate. The RAFT technique also has limitations in obtaining well-defined functionalization as not all polymer chains will have the desired end-functionalization due to the need for external polymerization sources. Odor and discoloration due to the sulfur-based control agents are also drawbacks of this technique. In addition, the ATRP and RAFT techniques both suffer from by-product contamination and product purification problems.

Thus, a need exists for a controlled method for preparing tailored polymers containing the PEG group that provides flexibility in their design but does not have these disadvantages.

The delivery of functional agents, which are defined herein as; molecules, bioactive molecules, ingredients, or compositions such as flavors, fragrances, pharmaceuticals or pesticides, agrochemicals such as herbicides, fungicides, or pesticides, dyes, and many others are an important aspect for nearly all applied sciences. Without the stabilization of a concentrated, easily transportable and processable form of the functional agent, delivery becomes unreliable and the agent will only rarely exhibit its beneficial properties at the predetermined place and time. Effective encapsulation is required in a wide range of applications in order to protect sensitive additives from degradation and to control their release, which will optimize their performance according to the required application.

There are many different encapsulation technologies apart from PEGylation available. One such available technique is to use amphiphilic block copolymers (polymers having hydrophilic and hydrophobic block segments). Amphiphilic block copolymers are well known to form micelles in aqueous solution making them suitable for encapsulation or solubilization of hydrophobic or water insoluble agents. Encapsulation technologies and specifically the use of amphiphilic block copolymers are described for example in U.S. Pat. Nos. 5,939,453, 6,638,994, US Patent Publications 2007/0160561, US2004/0010060, and 2005/0180922 the disclosures of which are incorporated herein by reference. These references describe amphiphilic polymers prepared by the aforementioned ATRP or RAFT methods and are limited by the drawbacks associated with these techniques (previously described above). Also described is a class of PEO based amphiphilic block copolymers made by living anionic polymerization techniques.

Living anionic polymerization suffers from several drawbacks, such as, poor copolymerization between polar and non-polar comonomers and the inability to use monomers that can be easily deprotonated. Therefore functional monomers cannot be directly incorporated and the copolymerization of monomer mixtures can be problematic and/or non-viable. This reduces the ability to tailor properties such as solubility, reactivity, and Tg. Furthermore, this process can be expensive, difficult or impractical to carry out on an industrial scale as bulk or emulsion techniques cannot be used, extremely pure reagents are necessary (even trace amounts of protic material inhibits polymerization), and an inert atmosphere is requisite.

These references either use techniques that are not amenable to tailoring specific properties through copolymerization, gradient copolymers, functionalization or fail to teach the significance of tailoring block composition or allowing for the formation of gradient compositions to control both agent solubility and agent release.

SUMMARY OF THE INVENTION

The invention relates to functionalized and/or tailored polymers formed by nitroxide mediated controlled radical polymerization (NM-CRP). In one aspect, the invention is a process for preparing polymers capable of PEGylating functional agents. In another aspect, the invention provides a process for tailoring functionalized non PEG-based polymers capable of binding to or encapsulating a functional agent. In another aspect, the invention provides a process for tailoring an amphiphilic block copolymer to allow for enhanced functional agent encapsulation and control over the agent release characteristics.

DETAILED DESCRIPTION OF THE INVENTION

Unless the context indicates otherwise, in the specification and claims, identified groups of materials also include mixtures of such materials. Unless otherwise specified, all percentages are percentages by weight and all temperatures are in degrees Centigrade (degrees Celsius).

Controlled Radical Polymerization

Polymers of the invention can be used to bind to or encapsulate functional agents. The invention describes a process for preparing these polymers and for tailoring them to allow for enhanced functional agent encapsulation and control over the agent release characteristics. By bind or bound is meant that the functional agent is covalently linked to the polymer. By encapsulated is meant that the functional agent is entrapped, but not covalently bound.

They are preferably prepared using Nitroxide-Mediated CRP (NM-CRP). NM-CRP allows for the synthesis of polymers containing specific and controlled functionality and/or tailored solubilities, which can aid in the binding to and/or encapsulation of a variety of functional agents and for controlling their release.

While it is apparent that various CRP approaches could be used to prepare these polymers, NM-CRP is preferred due to it's numerous advantages over the other known CRP techniques, such as ATRP and RAFT, in which the many limitations were previously described. NM-CRP allows for the use of a wide variety of monomers, including the use of acrylics, acrylamides, and especially acid functional acrylics. Another clear advantage of nitroxide-mediated CRP is that the nitroxide is generally innocuous and can remain in the reaction mix, while other CRP techniques often require the removal of the control compounds from the final polymer. Stringent purification of the reagents is not needed. Furthermore, functionalized alkoxyamines can be used to ensure 100% or nearly 100% of the formed polymers contain a functional group at either the chain end or in the center of the polymer chain.

NM-CRP involves the use of nitroxide mediators to control free radical polymerization, so that sequenced copolymers, including block copolymers, with well-defined structure can be prepared. NM-CRP is disclosed, for example, in U.S. Pat. Nos. 6,255,448; 6,569,967; and U.S. Pat. No. 6,646,079; the disclosures of which are all incorporated herein by reference. The polymerization can occur in bulk, solvent, and aqueous media, and can be used in existing equipment at reaction times and temperature similar to other free radical polymerizations.

In this process, the free radical polymerization process is controlled by the nitroxide, which is a stable free radical. Because the polymerization is controlled and the polymer is a living polymer, the process makes it possible to prepare block polymers in which the composition and chain length of each block is closely controlled by successive introduction of different monomers into the polymerization medium. In addition, the living nature of the polymerization makes it possible to prepare copolymers or gradient type polymers, which are homogeneous (i.e., all chains in a given reaction mixture have a similar compositional make up). Through this control, NM-CRP can yield block copolymers with precisely tailored compositions, molecular weights, functionalization, and architectures.

The mechanism for this control may be represented diagrammatically as below:

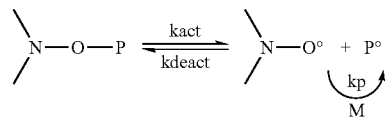

with M representing a polymerizable monomer and P representing the growing polymer chain. The key to the control is associated with the constants $K_{deact}$, $k_{act}$ and $k_p$ (T. Fukuda and A. Goto, Macromolecules 1999, 32, pages 618 to 623). If the ratio $k_{deact}/k_{act}$ is too high, the polymerization is blocked, whereas when the ratio $k_p/k_{deact}$ is too high or when the ratio $k_{deact}/k_{act}$ is too low though, the polymerization is uncontrolled. It has been found (P. Tordo et al., Polym. Prep. 1997, 38, pages 729 and 730; and C. J. Hawker et al., Polym. mater. Sci. Eng., 1999, 80, pages 90 and 91) that β-substituted alkoxyamines make it possible to initiate and control efficiently the polymerization of several types of monomers, whereas TEMPO-based alkoxyamines [such as (2',2',6',6'-tetramethyl-1'-piperidyloxy-)methylbenzene mentioned in Macromolecules 1996, 29, pages 5245-5254] control only the polymerizations of styrene and styrenic derivatives. TEMPO and TEMPO-based alkoxyamines are not suited to the controlled polymerization of acrylics.

Preparation of β-phosphorous nitroxide radicals useful as regulators of free radical polymerization is disclosed in US Patent Publication 2004/0077873, the disclosure of which is incorporated herein by reference.

The nitroxides have the general structure:

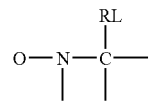

Where $R_L$ represents a mole weight of more than 15.

An exemplary β-phosphorous nitroxide radical useful for CRP is SG1, also known as, N-t-butyl-N-[1-diethylphosphono-(2,2,-dimethylpropyl)]nitroxide or (DEPN), which has the structure:

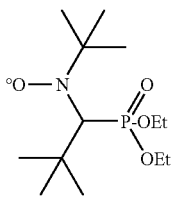

Specifically useful nitroxide compounds are alkoxyamines that combine the controller and initiator into one molecule. U.S. Patent Publication 2005/0065119, the disclosure of which is incorporated herein by reference, discloses alkoxyamines derived from β-phosphorylated nitroxides. The alkoxyamines have the general structure:

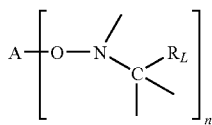

Where the alkoxyamine is obtained from β-substituted nitroxides of formula (I) wherein A represents a mono- or polyvalent structure and $R_L$ represents a mole weight of more than 15 and is a monovalent radical, and n≥1. The formation of polyvalent alkoxyamines of formula (I) can be obtained by the reaction of multifunctional monomers, such as, but not limited to, acrylate monomers and alkoxyamines at controlled temperatures. The multifunctional alkoxyamines of formula (I), wherein n≥2, may then be utilized to synthesize star and branched polymeric and co-polymeric materials from the monomer or monomers under consideration.

One exemplary useful compound is the alkoxyamine formed by linking the SG1 radical to an isobutyric acid radical (iBA-SG1 initiator), whose structure is shown below.

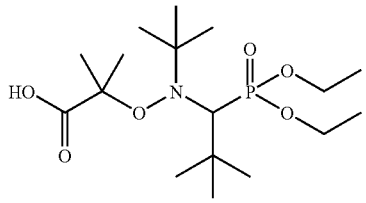 [SMILES: CCOP(=O)(OCC)C(N(OC(C)(C)C(=O)O)C(C)(C)C)C(C)(C)C]

This initiator/controller is suitable for a wide variety of monomers, including acrylates and functional acrylics, such as acrylic acid. This compound is commercially available from Arkema Inc. as the BlocBuilder® controller for free radical polymerization.

The use of the alkoxyamine BlocBuilder® controller has an inherent advantage as the initiating fragment has a carboxylic acid functional group which is incorporated directly into the polymer chain and can be further utilized as a chemical handle to either directly attach to a functional agent or to serve as a point for further chemical modification.

If BlocBuilder® controller is used directly, the acid functionality will reside on one chain end. The acid functional chemical handle is important as it provides a site for further transformation to a wide variety of functionality. For example, the acid can be readily converted to any number of useful functional groups, and without limiting them, many are disclosed in WO 2006/003352. U.S. Pat. No. 7,214,810 discloses many examples of converting the acid functionality of BlocBuilder® controller and polymers which are end-functionalized by the acid moeity of BlocBuilder® controller. Many other conversion techniques will be evident to those skilled in the art.

The use of BlocBuilder® controller gives the ability to have a high degree of end-functionalized chain ends. Since the functional moiety serves as the initiation source, theoretically 100% of the chains should be end-functionalized. This high degree of functionalization specifically eliminates the often undesirable production of chains telechelic in nature (which are formed in the anionic process), and non-functional chains which are produced by the RAFT process. Anionic formed polymers typically contain greater than 5% of the telechelic polymer. These can often lead to unwanted crosslinking reactions.

Of course, non-functional alkoxyamines that contain SG1 including, for example, MONAMS, a mono-functional initiator, and DIAMS, a di-functional initiator can also be used. The structures of these initiators are shown below:

SG1-CH(CH$_3$)—C(O)OCH$_3$ (SG1-CH(CH$_3$)—C(O)O (CH$_2$)$_3$)$_2$

MONANS  DIAMS iBA-SG1 initiator when heated separates into two free radicals, one of which initiates polymerization and one of which, the SG1 nitroxide radical, reversibly terminates polymerization. The SG1 nitroxide radical dissociates from methacrylates above about 25° C. and disassociates from acrylates and styrenics approximately above 80 and 70° C. respectively. Thus iBA-SG1 can be reacted with an acrylate monomer at temperatures >25° C. and <75° C. in a 1:1 ratio to form a functionalized adduct.

The use of an alkoxyamine eliminates the need for an external initiation source (such as an organic peroxide or a diazo compound), though in some cases, a peroxide may be introduced to obtain a mixture of traditional free radically produced polymer and controlled polymer or a peroxide might be used at the end of the reaction to "chase" the residual monomer. Typically, a monofunctional alkoxyamines is used to synthesize an AB type block copolymer. A difunctional alkoxyamine is typically used to produce an ABA triblock copolymer. However, a triblock copolymer can also be made from a monofunctional alkoxyamine by first reacting monomer A, then monomer B, then switching back to monomer A. Using this methodology segmented ABABA type polymers can be formed as well as multiblock polymers containing several distinct monomer segments, such as ABC and ABCD as will be evident to those skilled in the art. Polymers made by this process will have nitroxide end groups. They can remain on the end of the polymer chains or be removed by an additional processing step.

Another process describes the preparation of multimodal polymers where at least one of the monomers under consideration is subjected to free radical polymerization in the presence of several alkoxyamines comprising the sequence of formula (I), wherein n is a non-zero integer and the alkoxyamines exhibit different values of n.

Functional agent binding or encapsulating polymers made by NM-CRP of the current invention can be described by three general classes of polymers; 1) tailored PEG-based functionalized polymers used for the PEGylation of functional agents, 2) non-PEG-based tailored functionalized polymers, capable of binding to or encapsulating a functional agent and, 3) tailored amphiphilic block copolymers, including functionalized and non-functionalized and PEG-based and non PEG-based that allow for both enhanced encapsulation and control over functional agent release characteristics. General descriptions of each class are described below, but are not meant to be limiting as will be evident to those skilled in the art.

Class 1 consists of PEG-based functionalized polymers made by NM-CRP used for the PEGylation of functional agents. One preferred class of functional agents includes; bioactive molecules, such as proteins, peptides, antibody fragments, oligonucleotide, and the like for use as drugs.

PEG-based polymers includes any polymer which contain polyethylene glycol units, either in the polymer backbone or in backbone side chains, as will be known to those skilled in the art. Preferred PEG-based polymers of the current invention are derived from monomers which are alkoxy polyethers, such as poly(alkyleneglycol). An example of these monomers include, polyethylene glycol acrylate and polyethylene glycol methacrylate with the structure given below and denoted as monomer (1):

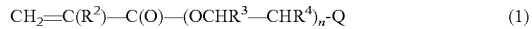
$$CH_2=C(R^2)-C(O)-(OCHR^3-CHR^4)_n-Q \quad (1)$$

in which $R^2$ is hydrogen or methyl and n is an integer from 1 to 400. $R^3$ and $R^4$ are preferably hydrogen, but n can also represent a side chain containing a mixture of repeat units of ethylene oxide and propylene oxide. That is, a fraction of the repeat units have $R^3$ and $R^4$ as hydrogen and the remaining $R^3$ and $R^4$ represent a hydrogen and a methyl group. Q can be a hydroxyl group, a methoxy group, an alkyl group, or other group. Q can also be L which is a linking group for attachment of a biologically-active molecule (M) or L'M a biologically-active molecule attached with a linking group in which L' is the linking group.

One example of a preferred monomer is when both $R^3$ and $R^4$ are preferably hydrogen and n is preferably between 3 and 110 as shown by the structure below and denoted as monomer (2):

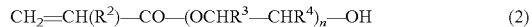
$$CH_2=CH(R^2)-CO-(OCHR^3-CHR^4)_n-OH \quad (2)$$

in which —OH is the linking group. Alternatively the linking group may be prepared by derivatization of monomers of this structure.

By functionalized as defined in the invention is meant that the polymer contains a linking group L which is capable of linking to a functional agent (FA), to create an L'FA or L'M group. The functionalization can come from the monomer described in (1), the initiating fragment of the alkoxyamine, or it can be introduced via a functionalized comonomer such as monomer (2) or acrylic acid or hydroxyethyl acrylate, etc. The polymer can contain more than one functional group. In one preferred embodiment the polymer contains only 1 L group. The functional groups derived from the monomers or initiating fragment of the alkoxyamine can be utilized as linking groups L by themselves or be readily modified to a linking group through traditional chemistries as previously mentioned.

The polymers of class 1 may contain only monomer repeat units which contain polyethylene glycol units, denoted as; pure PEG-based polymers, or they can contain monomers of non-polyethylene glycol units; denoted as; PEG-based copolymers. These monomers can be chosen from any olefinic monomer capable of undergoing free radical polymerization as will be evident to those skilled in the art.

Examples of useful monomers include, but are not limited to acrylics, such as acrylic acid; methacrylic acid; alkyl esters and mixed esters of (meth)acrylic acid; acrylamide; methacrylamide; N- and N,N-substituted (meth)acrylamides; maleic acid, fumaric acid, crotonic acid, itaconic acid and their corresponding anhydrides; carbonyl halides; amides, amidic acids, amidic esters, and the full and partial esters thereof, and mixtures thereof. Useful non-acrylic comonomers include ethylenically unsaturated monomers including, but not limited to, anhydrides, acrylonitriles, vinyl esters, alpha-olefins, dienes, substituted or unsubstituted mono and dialkyl esters of unsaturated dicarboxylic acids, vinyl aromatics, substituted vinyl aromatics, cyclic monomers, monomers containing alkoxylated side chains, sulfonated monomers, and vinyl amide monomers.

When the application is for the delivery of bioactive or therapeutic agents, the free radical polymerizable comonomers are chosen such that they can be co-polymerized by NM-CRP and do not adversely affect either the formation or the properties, such as water solubility, bio-acceptability, and/or bioactivity, of the resulting PEGylated bioactive molecule. Monomers such as acrylic acid and methacrylic acid and their salts, such as the potassium, sodium, lithium, ammonium and substituted ammonium salts; propylene glycol monoacrylate; propylene glycol monomethacrylate; vinyl pyrollidone, 1,4-butanediol monoacrylate; and 1,4-butanediol monomethacrylate and others are examples of potential comonomers.

The use of the alkoxyamine BlocBuilder® controller has an inherent advantage as the initiating fragment has a carboxylic acid functional group which is incorporated directly into the polymer chain end and can serve as a linking group L. In the absence of any other functional monomers, it provides for a polymer chain having exactly 1 linking group located at the chain end. This is a preferred embodiment of the disclosure. As previously mentioned, the acid functional L group can be readily transformed into a wide variety of functional L moeities The following description is meant to be representative of the type of class 1 materials which can be synthesized by NM-CRP, but is not to be considered limiting.

Monomer (1) or mixtures of monomer (1) can be polymerized using BlocBuilder® controller to form a comb type pure PEG-based polymer which contains a carboxylic acid group at the chain end. This polymer can be further functionalized through the Q group or the Q groups can be non functional (e.g., methoxy groups). In a preferred embodiment, the Q groups are not linking groups and the carboxylic acid group on the chain end serves as the linking group L or is modified to another form of linking group.

Another type of preferred controlled structure would contain only one unit of the monomer (1). This can be achieved by reacting an alkoxyamine such as BlocBuilder® controller with monomer (1) in 1-to-1 ratio (or slight excess of BlocBuilder® controller at controlled temperatures). This yields a low Mw end functionalized PEG-based oligomer.

It is also possible to bind the alkoxyamine directly to the functional agent prior to carrying out the polymerization as will be evident to those skilled in the art. Conducting the NM-polymerization directly on the delivery material in place of post reacting the polymer with the delivery material increases the binding efficiency. This route is especially attractive for an alkoxyamine such as BlocBuilder® controller which contains a functional linking site. This functional group can by itself act as a linking group L' or it can be readily modified to a linking group L' through traditional chemistries. Thus the linking group can be tailored to fit the desired chemistry required for the target molecule linking. This type of process route is another preferred method for producing a controlled structure. ATRP is limited in this route, as the subsequent processing step to remove the metallic impurities can damage the linked delivery material.

Monomer (1) can also be copolymerized with an additional monomer or monomers that can undergo addition polymerization to form gradient type PEG-based copolymers. When comonomers containing functional groups are used, these can be utilized as linking groups by themselves, or be readily modified. The copolymerization via NM-CRP technology ultimately allows one to tailor the final end use properties of the polymers which are exploited for binding/encapsulation. For example, hydrophobic monomers can be copolymerized with the PEG-based monomer, which in the case of PEGylated drugs will ultimately vary the hydrodynamic volume of the encapsulated particle and vary the stability, solubility, toxicity, and/or the drug retention time of a drug that has been covalently attached to the copolymer.

PEG-based copolymers can be produced that contain 2 different types of L groups, wherein each type of L group has binding affinity for a different functional agent, leading to a polymer that contains two or more different active molecules. For example, if monomer (1) contains a linked functional agent it can be co-polymerized with other functionalized monomers containing a different functional agent and optionally non-functionalized comonomers, the non functionalized comonomers can be PEG-based on non-PEG based. By proper control of the amount of monomer (1) and the amount of co-monomer or co-monomers in the controlled radical polymerization it is possible to control the molecular weight, and solubility of the final PEGylated polymer and the amount of biologically-active molecule(s) in the final PEGylated bioactive polymer. Furthermore, the spacing and concentration of the branches or monomers containing the functional agent can be controlled via copolymerization with non-functional monomers. By processes of this type, it is possible to control the amount, the type, and the location of the functional agent in the PEG-Based copolymers.

Therefore an important benefit of the present invention is the ease in which the specific composition and architecture of the corresponding (co)polymers can be tailored accordingly based on the intended functional agent to be delivered.

Linking Groups

Linking groups for the attachment of bioactive molecules to polyethylene glycol and to polyoxyethylated polyols are well know to those skilled in the art. Any of the activating groups of the known derivatives of PEG can be used. For example, the succinimidyl ester can be attached to protein amino groups. However, there are a wide variety of functional moieties available for activation of carboxylic acid polymer moieties for attachment to various surfaces and molecules. Examples of active moieties used for biological and biotechnical applications include trifluoroethylsulfonate, isocyanate, isothiocyanate, active esters, active carbonates, various aldehydes, various sulfones, including chloroethylsulfone and vinylsulfone, maleimide, iodoacetamide, and iminoesters. Active esters include N-hydroxylsuccinimidyl ester. Active carbonates include N-hydroxylsuccinimidyl carbonate, p-nitrophenylcarbonate, and trichlorophenylcarbonate.

Linking groups are disclosed in Thompson, U.S. Pat. No. 6,552,170, the disclosure of which is incorporated herein. A useful activating group that can be used for selective coupling with thiol moieties instead of amino moieties on molecules and surfaces is the vinyl sulfone moiety described in Harris, U.S. Pat. No. 5,446,090, the disclosure of which is incorporated herein by reference.

Attachment of bioactive molecules to polyethylene glycol and to polyoxyethylated polyols using the disuccinimidylcarbonate (bis-succinimidyl carbonate or DSC) linking group is disclosed in U.S. Pat. No. 5,281,698, the disclosure of which is incorporated herein by reference. The reaction of DSC with a PEG that has a free hydroxyl group is carried out in an inert solvent, such as methylene chloride or chloroform using a basic catalyst such as pyridine or 4-dimethylaminopyridine. Any precipitate that forms is filtered off. The active PEG ester precipitated from the reaction mixture by the addition of diethyl ether, filtered off, washed with diethyl ether, and, if necessary, redissolved and reprecipitated.

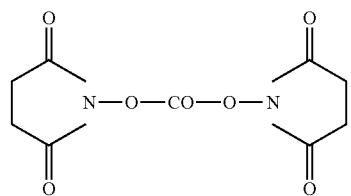

Disuccinimidylcarbonate (DSC)

In the present invention, monomers that contain a linking group may be prepared by this procedure.

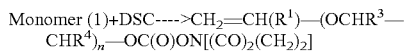

Class 2 consists of tailored non PEG-based functionalized polymers made by NM-CRP used for the binding or encapsulation of functional agents. This class of polymer can be prepared using the same techniques and processes as the class 1 polymers, with the exception being PEG-Based monomers, such as monomer (1) and monomer (2) are not used. The solubility of the prepared functional polymers can be tailored based on monomer composition. Two examples of class 2 non PEG-based functional polymers used for encapsulation or binding of functional agents are water soluble or hydrophilic functional polymers and organic soluble or hydrophobic functional polymers. Of course one can attain a polymer with an affinity for both media by copolymerizing a mixture of the two monomer types.

By hydrophilic polymers is meant that the polymer or copolymer has an affinity for water. By "hydrophilic" or "hydrophilic polymer" as used herein is meant the polymer block segment is water soluble, water dispersible, or generally capable of absorbing and/or transmitting water. The hydrophilic polymer could be a hydrophilic homopolymer, a random copolymer containing one or more hydrophilic monomers, or a random copolymer containing one or more hydrophilic monomers with one or more hydrophobic monomers. Ethylenically unsaturated monomers useful in forming hydrophilic polymers include but are not limited to, acrylic acid, methacrylic acid, and the salts, esters, anhydrides and amides of methacrylic and acrylic acid; dicarboxylic acid anhydrides; carboxyethyl acrylate; hydrophilic derivatives of styrene; and acrylamides. Specific useful monomers include, but are not limited to maleic anhydride, maleic acid, substituted maleic anhydride, mono-ester of maleic anhydride, itaconic anhydride, itaconic acid, substituted itaconic anhydride, monoester of itaconic acid, fumaric acid, fumaric anhydride, fumaric acid, substituted fumaric anhydride, monoester of fumaric acid, crotonic acid and its derivatives, acrylic acid, methacrylic acid, dimethylacrylamide, diethyl acrylamide, n-isopropylacrylamide, dimethylaminoethyl acrylate, diethylaminoethylacrylate, styrene sulfonic acid, acrylamido 2-methyl 2-propane sulfonate, vinylpyrrolidone, 2-carboxyethyl acrylate, methyl acrylate, ethyl acrylate, 2-methoxyethyl acrylate, hydroxyethyl acrylate, and hydroxyethyl methacrylate. Salts of the acid monomers and quaternized versions of the amines are also anticipated in the invention.

By hydrophobic polymers is meant that the polymer or copolymer is not water-soluble. By "hydrophobic" and "hydrophobic polymer" as used herein is meant the polymer block segment is non-soluble or dispersible in water. The hydrophobic polymer could be a hydrophobic homopolymer, a random copolymer containing one or more hydrophobic monomers, or a random copolymer containing one or more hydrophobic monomers with one or more hydrophilic monomers. Examples of ethylenically unsaturated monomers useful in forming the hydrophobic polymers include, but are not limited to, styrene, hydrophobic derivatives of styrene, conjugated dienes, $C_{3-30}$ straight or branched alkyl, and aryl (meth)acrylates, olefins, fluorine-containing monomers, and silicon-containing monomers Specific examples of the hydrophobic monomers include styrene; alpha-methyl styrene, lauryl methacrylate (or other long chain alkyl acrylates or methacrylates, e.g., $C_6$-$C_{30}$ alkyl esters 2-ethylhexyl acrylate and 2-ethylhexylmethacrylate, octyl acrylate, and octyl methacrylate, decyl acrylate and decyl methacrylate, etc., 1,1-dihydroperfluoroalkyl acrylates and methacrylates of the general structure, $CF_3(CF_2)_nCH_2OCOC(R)=CH_2$, in which R is hydrogen or methyl and n is typically 2 to 20, hexafluorobutyl acrylate, triisopropylsilyl acrylate, isobornyl acrylate, isobornyl methacrylate, butadiene, isoprene, methylmethacrylate, t-butyl acrylate and t-butyl methacrylate.

The aforementioned lists of hydrophilic and hydrophobic monomers contain a variety of functionalized and non-functionalized monomers. The functionalized monomers provide the L group which can be used to bind to functional agents of the current invention to create a L'FA linkage, and in the case where all non-functionalized monomers are used, the L group provided by the alkoxyamine can be utilized as was previously described in the class 1 polymer section.

Class 3 consists of tailored amphiphilic block copolymers made by NM-CRP, including functionalized and non-functionalized and PEG-based and non PEG-based that allow for both enhanced encapsulation and control over functional agent release characteristics.

By "block copolymer" as used herein means di-blocks, tri-blocks, or multiblocks, graft block copolymers, branched block copolymers (also known as linear star polymers), as will be evident to those skilled in the art. Also included by "block copolymer" as used herein are gradient polymers or gradient block copolymers. Gradient polymers are linear or branched copolymers made by a controlled polymerization process whose composition changes along the polymer chains, potentially ranging from a random to a block-like structure.

When a copolymer segment is synthesized using a controlled radical polymerization (CRP) technique such as nitroxide-mediated polymerization, it is often termed a gradient or 'profiled' copolymer. This type of copolymer is different than a polymer obtained by a traditional free radical process and will be dependant on the monomer composition, control agent, and polymerization conditions. For example, when polymerizing a monomer mix by traditional free radical polymerizations, a statistical copolymer is produced, as the composition of the monomer mix remains static over the lifetime of the growing chain (approximately 1 second). Furthermore, due to the constant production of free radicals throughout the reaction, the composition of the chains will be non-uniform as monomer concentration will fluctuate. During a controlled radical polymerization the chains remain active throughout the polymerization, thus the composition is uniform and is dependant on the corresponding monomer mix with respect to the reaction time. Thus in a two monomer system where one monomer reacts faster than the other, the distribution or 'profile' of the monomer units will be such that one monomer unit is higher in concentration at one end of the polymer segment.

Each block of the block copolymers may itself be a homopolymer, a copolymer (where copolymer includes terpolymer and other combinations of two or more different monomers), or a gradient polymer. Gradient block copolymers can be formed for example by allowing unreacted monomer from a $1^{st}$ block to continue to react in the formation of a second block. Thus in an A-B block gradient copolymer, the A block is formed first. When the monomer(s) for the B block are added, the unreacted A block monomer(s) is kept in the mixture to react leading to an A-B block copolymer with a gradient of the A block in the B block. Gradient block copolymers are the preferred block copolymers of the invention as specific properties through gradient compositions and/ or well-placed functionalization allow for control over both agent solubility and agent release. Preferred gradient block polymers are A-B diblock and A-B-C or A-B-A triblock copolymers.

By amphiphilic block copolymers is meant that at least one segment is compatible with the functional agent and at least one segment is not compatible. For example when a hydrophobic functional agent is mixed with an AB block copolymer containing a hydrophilic A block and a hydrophobic B block.

Amphiphilic block copolymers containing hydrophilic and hydrophobic segments are well known to form micelles in aqueous solution making them suitable for encapsulation or solubilization of hydrophobic or water insoluble agents. However, previously disclosed materials suffer from drawbacks brought upon by the method by which they were prepared. NM-CRP can overcome these limitations. Furthermore the polymers of this invention further describe the added benefit of tailored composition, through gradients and functionalization.

Amphiphilic hydrophilic/hydrophobic block copolymers are preferred block copolymers of the present invention. The hydrophilic block segment(s) can be PEG-based or non PEG-based, functionalized or non functionalized.

The ability to use copolymerization to make block copolymer structures which can be pure or gradient in nature by virtue of the NM-CRP technology ultimately allows one to tailor the final end use properties of the polymers and also control the amount and placement of functional sites which are exploited for binding or encapsulation. The functional sites can be used to bind to a functional agent through a covalent bond or use other non-covalent forces, such as hydrogen bonding which will be evident to those skilled in the art. If functional groups are not present, the encapsulation can simply be attained by entrapment by tuning the solubility. For example when a hydrophobic functional agent is mixed with an AB block copolymer containing a hydrophilic A block and a hydrophobic B block, the drug will be encapsulated in the hydrophobic B phase of the material.

The use of gradient of block systems can allow for the preparation of polymers with controlled solubilities allowing block copolymers to be designed for specific functional delivery agents. Also, one can control the release of functional agents by tailoring the composition of the block segments. For example, in the case of an ABC triblock copolymer in which A is hydrophillic and B and C are not hydrophilic, when the polymer is put into water it will form micelles with an outer layer of the A block, a middle layer of the B block and a core of the C block. If the C block is most compatible with the functional agent it will primarily reside or be encapsulated there. One can tailor the B segment to control its release. As the functional agent diffuses out of the C segment it must pass through B. B can be tailored to allow the agent to pass slowly or quickly. One method is by simply altering the solubility of the B layer with respect to the functional agent.

Therefore an important benefit of the disclosed invention is the ease in which the specific composition and architecture of the corresponding block copolymers can be tailored accordingly based on the intended functional agent to be delivered.

Another example of controlled release is to use crystalline block segment(s). For example, using an AB block copolymer, which has a hydrophilic A segment to allow for aqueous dispersion and micelle formation and a hydrophobic B segment compatible with the functional agent, the B segment can be tailored to be crystalline by using monomers such as lauryl methacrylate or stearyl methacrylate. Thus when the polymer is heated and the crystalline B segment melts, the functional agent will be able to diffuse or release freely. Thus, the crystallinity is a tool for controlling the functional agent release. The B segment can be a mixture of crystalline monomers or contain some fraction of non-crystalline monomers to effectively tailor the melting temperature.

The block copolymers can have 1 segment as described in the class 1 or 2 polymers that contains L'M or L'FA linkage(s) and a second block that has no functional groups. The non-functional segment can be tailored to give solubility in the desired delivery media.

Another example of a amphiphilic block copolymer would contain only one unit of the monomer of type (1) achieved by reacting an alkoxyamine such as BlocBuilder® controller with monomer (1) in a 1-to-1 ratio at controlled temperatures. Since this material has a nitroxide group on the opposite end, it can be further polymerized with a $2^{nd}$ monomer(s) to produce a block copolymer. The $2^{nd}$ block segment will be comprised of a block capable of binding or encapsulating a functional agent as previously described.

As described in the class 1 and 2 type polymers, it is also possible to bind the alkoxyamine to the functional agent or bioactive material prior to carrying out the block copolymer synthesis.

Examples of monomers useful in the hydrophilic block segment may include acrylic acid, methacrylic acid, methoxyethyl acrylate, maleic anhydride, 2-hydroxyethyl acrylate, 2-hydroxyethyl methacrylate, polyethyleneglycol acrylate, polyethyleneglycol methacrylate, N,N,dimethylacrylamide, styrene sulfonate or mixtures thereof. Examples of monomers useful in the hydrophobic block segment may include esters of acrylic and methacrylic acid containing hydrogenated or fluorinated C1 to C24 alcohols, styrene, dienes or mixtures thereof. Hydrophobic monomers can be used in the hydrophilic blocks and hydrophilic monomers can be included in the hydrophobic blocks.

INDUSTRIAL APPLICABILITY

Effective encapsulation is required in a wide range of applications in order to protect sensitive additives from degradation and to control their release, which will optimize their performance according to the required application. The delivery of functional agents, which are defined as; molecules, bioactive molecules, ingredients, or compositions such as flavors, fragrances, pharmaceuticals or pesticides, agrochemicals such as herbicides, fungicides, or pesticides, dyes, and many others can be carried out using the polymers of the current invention. The tailored block copolymers allow for stabilization, concentration, ease of transport and processing form of the functional agent, thus delivery will become reliable and the agent will exhibit its beneficial properties at the desired location and time. Applications include but are not limited to drug delivery, agrochemical delivery, cosmetic delivery, fragrance delivery, and others.

Biologically active agents that can be usefully modified by attachment to the polymers of the invention include, but are not limited to, pharmaceuticals, vitamins, nutrients, nucleic acids, amino acids, polypeptides, proteins, enzymes, enzyme co-factors, steroids, carbohydrates, organic species such as heparin, metal containing agents, receptor agonists, receptor antagonists, receptors or portions of receptors, cell surface molecules, antigens, haptens, targeting groups that can direct a compound to a location in a biological system, and chelating agents, such as hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. Biologically active agents also include numerous proteins and enzymes that can be usefully modified by attachment to the polymers of this invention. Glycosylated polypeptides and synthetically modified proteins may also be used. Proteins and enzymes can be derived from animal sources, humans, microorganisms, and plants and can be produced by genetic engineering or synthesis. Representatives include, for example: cytokines such as various interferons (e.g., interferon-α, interferon-β, interferon-γ, interleukin-2 and interleukin-3), hormones such as insulin, growth hormone-releasing factor (GRF), calcitonin, calcitonin gene related peptide (CGRP), atrial natriuretic peptide (ANP), vasopressin, corticotropin-releasing factor (CRF), vasoactive intestinal peptide (VIP), secretin, α-melanocyte-stimulating hormone (α-MSH), adrenocorticotropic hormone (ACTH), cholecystokinin (CCK), glucagon, parathyroid hormone (PTH), somatostatin, endothelin, substance P, dynorphin, oxytocin and growth hormone-releasing peptide, tumor necrosis factor binding protein, growth factors such as growth hormone (GH), insulin-like growth factor (IGF-I, IGF-II), β-nerve growth factor (β-NGF), basic fibroblast growth factor (bFGF), transforming growth factor, erythropoietin, granulocyte colony-stimulating factor (G-CSF), granulocyte macrophage colony-stimulating factor (GM-CSF), platelet-derived growth factor (PDGF) and epidermal growth factor (EGF), enzymes such as tissue plasminogen activator (t-PA), elastase, superoxide dismutase (SOD), bilirubin oxydase, catalase, uricase and asparaginase, other proteins such as ubiquitin, islet activating protein (IAP), serum thymic factor (STF), peptide-T and trypsin inhibitor, and derivatives thereof. Biologically active agents also include small molecules that, when attached to the polymers of this invention, can be expected to show enhanced solubility in either aqueous or organic solvents. Lipids and liposomes attached to the derivative of the invention can be expected to show long blood circulation lifetimes. The polymers of the invention could be attached to various forms of drugs to produce prodrugs. Small drugs having the multisubstituted derivative attached can be expected to show altered solubility, clearance time, targeting, and other properties.

EXAMPLES

These examples are representative of the classes of polymers readily prepared by NM-CRP and useful as per the present invention. These examples are not meant to be inclusive as will be evident to those skilled in the art. The controlled architecture amphiphilic block copolymers were synthesized using the following generic protocol. Molecular weights were targeted by manipulating the monomer to initiator concentration ([M]/[I]). Therefore a targeted molecular weight could be achieved by setting the [M]/[I] ratio, and then carrying out the polymerization to the desired conversion necessary to reach the target molecular weight. Monomer conversion was conveniently monitored by gas chromatography (GC) analysis, flash devolitization, or extraction of the un-reacted monomer. The polymer examples were run neat or in solution. Typical solvents used included, dioxane, n-methylpyrrolidinone, dimethylacetamide, dimethylformamide, tert-butyl alcohol, n-butyl alcohol, toluene, ethyl benzene, acetone, methyl acetate, ethyl acetate, propyl acetate, butyl acetate, ethanol, cyclohexanone, cyclopentanone and methyl ethyl ketone. Polymerizations were carried out at ambient pressures or run under nitrogen pressure up to 60 psi. Polymerizations were run in standard polymerization vessels both with and without shearing capacity, although adequate mixing capabilities were preferred.

As a general procedure, specific diblock copolymer compositions are prepared by various traditional monomer addition and polymer isolation protocols, as generically described below and evident to those skilled in the art, dependant on the desired final block composition.

For example, a pure block copolymer is prepared by isolating the pure 1st block by precipitation techniques or by evaporating the residual monomer upon completion of the first block synthesis, followed by the addition of a second monomer composition different from the first. This second monomer composition then undergoes polymerization.

Profiled block copolymers were synthesized by polymerizing a mixture of two or more monomers. This mixture could result, for instance, by adding a second monomer to the initial polymerization medium prior to evaporation of the residual first monomer, or a multi-monomer mix could be polymerized as a first block, or a multi-monomer mix could be added to an isolated pure first block.

Pure gradients were formed from a mix of monomers in which one or more monomers reacts much faster than the other(s). The resultant gradient polymer will contain the reactive monomer heavily concentrated at one end of the polymer chain.

Gradient block copolymers were formed by allowing un-reacted monomer from a $1^{st}$ block to continue to react in the formation of a second block. Thus in an A-B block gradient copolymer, the A block is formed first. When the monomer(s) for the B block are added, the un-reacted A block monomer(s) is kept in the mixture to react leading to an A-B block copolymer with a gradient of the A block in the B block.

The synthesis of the copolymers of the invention as described above is further illustrated by reference to examples 1, 2 and 3 below (one detailed example of each class of polymer) and the results in Table 1. Other copolymers of this invention can be prepared in an analogous manner, as it will be evident to those skilled in the art.

TABLE 1

All polymers in Table 1 were prepared using methods analogous to examples 1, 2, and 3 and using the methods described above.

| Example | Block A | Block B | Mn A (kg/mol) | Mn B (kg/mol) | Class |
|---|---|---|---|---|---|
| 1 | MA/PEGm 46%/AA6% | | 6.4 | | 1 |
| 2 | MA/PEGm 46%/AA6% | MMA | 6.4 | 95.8 | 3 |
| 3 | EA/DMA26% | | 14.2 | | 2 |
| 4 | EA/PEGm30% | | 9.5 | | 1 |
| 5 | PEGa | | NM | | 1 |
| 6 | ZTAN | | 2.3 | | 2 |
| 7 | S/MEA46% | | 15.4 | | 2 |
| 8 | ZTAN | DMA | 5 | NM | 3 |
| 9 | MA/PEGm 34% | BA | 21.8 | 11.7 | 3 |
| 10 | EA/DMA26% | LMA | 14.2 | 26.1 | 3 |
| 11 | MA | LMA | 12.0 | 25.0 | 3 |

All polymers were prepared using BlocBuilder® controller. Block A describes the monomer(s) used in the synthesis of the $1^{st}$ block. In the case of homopolymers or gradient copolymers, the $1^{st}$ block is the only block. Block B describes the primary monomer used in the $2^{nd}$ block synthesis and as described in the synthesis examples below, the endblock may or may not contain some level of monomer carryover from the $1^{st}$ block synthesis as well. In the event that a significant amount (>10 wt %) of carryover monomer exists in the B block, the approximate wt % is denoted. The approximate number average molecular weight (Mn) for the A and B blocks are denoted. The Mn values were calculated based on starting [M]/[I] ratios and the measured monomer conversion data. When monomer conversion data was unavailable, the GPC Mn was used (relative to PS standards). The class of polymer (as described in the text) is denoted in the last column. NM denotes not measured. The monomer abbreviations are: MA=methyl acrylate, MMA=methylmethacrylate, EA=ethyl acrylate, S=styrene, LMA=lauryl methacrylate, BA=butyl acrylate, MEA=2-methoxyethyl acrylate, AA=acrylic acid, DMA=N,N dimethylacrylamide, ZTAN=Fluorinated acrylate supplied by DuPont, PEGa=polyethyleneglycol acrylate, and PEGm=polyethyleneglycol methacrylate.

All polymers in Table 1 were prepared using methods analogous to examples 1-3 below:

Example 1

A living first block terpolymer of poly(methylacrylate)-co-poly(polyethyleneglycol methacrylate)-co-poly(acrylic acid) was prepared using the alkoxyamine BlocBuilder® controller (iBA-DEPN). The polyethyleneglycol methacrylate had an average Mn of 475 g/mole and was supplied from Aldrich. 2.84 g of BlocBuilder® controller (7.4 mmol) was added to 40.7 g of methyl acrylate (0.473 mol) and 28.8 g of PEG methacrylate (60.5 mmol) and 4.5 g acrylic acid (62.5 mmol). The mixture was bubbled with nitrogen for 10 minutes before adding to a 250 mL glass reactor. The reactor was sealed, stirring started, and heated to 100° C. for 1 hour and then increased to 115° C. for 2 additional h's, at which point the methyl acrylate and acrylic acid were approximately 60% converted to polymer, and the PEG methacrylate was approximately 80% converted to polymer, corresponding to an Mn of approximately 6.4 kg/mol. The GPC gave a PDI of 1.2.

Example 2

To form an amphiphilic diblock, 7.73 g of the polymer from example 1 was mixed with 70.9 g methyl methacrylate (0.709 mol). The mixture was bubbled with nitrogen for 10 minutes before adding to a 250 mL glass reactor. The reactor was sealed, stirring started, and heated to 107° C. for 80 minutes at which point the methyl methacrylate was approximately 54% converted to polymer, corresponding to an Mn of approximately 95.8 kg/mol. The GPC gave a PDI of 2.0.

Example 3

To form a hydrophilic copolymer with a linking group L on the chain end, 0.77 g of BlocBuilder® controller (2.02 mmol) was added to 10.05 g of dimethylacrylamide (0.101 mol) and 30 g of ethyl acrylate (0.30 mol). The solution was placed into a vial with a magnetic stir bar and degassed. The vial was then heated to 115° C. and allowed to react for 180 minutes, until approximately 70% conversion of the ethyl acrylate was obtained and 75% conversion of the dimethylacrylamide, corresponding to an Mn of approximately 14.2 kg/mol. The GPC gave a PDI of 1.3.

Having described the invention, we now claim the following and their equivalents.

The invention claimed is:

1. A composition comprising:
   a functional agent, and
   a tailored polymer comprising polyethylene glycol(meth)acrylate monomer units bound to or encapsulating said functional agent wherein said tailored polymer is formed via beta-phosphorous nitroxide mediated controlled radical polymerization, and wherein said tailored polymer contains beta-phosphorous nitroxide end groups.

2. The composition of claim 1 wherein said tailored polymer is a functional polyethylene glycol containing polymer wherein said functional agent is bound to the tailored polymer via one or more linking groups.

3. The composition of claim 1 wherein said functional agent is a bioactive material and said tailored polymer is a functional polyethylene glycol containing polymer.

4. The composition of claim 1 wherein said tailored polymer is a functional polyethylene glycol containing polymer having at least one end group comprising a linking group wherein said linking group is derived from alkoxyamines used as polymerization initiators.

5. The composition of claim 1 wherein said tailored polymer is an amphiphilic block copolymer.

6. The composition of claim 5 wherein said amphiphilic block copolymer contains at least one block segment which is a gradient copolymer.

7. The composition of claim 6 wherein said functional agent is selected from agrochemical agents, pharmaceutical agents, flavor or fragrance agents or cosmetic agents.

8. The composition of claim 1 wherein said tailored polymer is an amphiphilic block copolymer comprising at least one block segment which can crystallize and said functional agent is encapsulated by, but not covalently bound to said tailored polymer.

9. The composition of claim 8 wherein said at least one block segment which can crystallize is crystallized and is a gradient copolymer.

10. The composition of claim 8 wherein said amphiphilic block copolymer comprises at least one hydrophilic block segment and at least one hydrophobic block segment.

11. The composition of claim 1 wherein said tailored polymer is an amphiphilic block copolymer comprising at least one block segment which is a gradient copolymer and said functional agent is encapsulated by, but not covalently bound to said tailored polymer.

12. The composition of claim 1 wherein said tailored polymer is an amphiphilic block copolymer containing at least one hydrophilic block segment and at least one hydrophobic block segment.

13. The composition of claim 12 wherein:
   at least one segment of said tailored polymer is a gradient copolymer;
   said functional agent is hydrophobic or water insoluble; and
   said functional agent is encapsulated but not covalently bound to said tailored polymer.

14. The composition of claim 12 wherein said tailored polymer is an ABC triblock copolymer.

15. The composition of claim 14 wherein one or more block segments is gradient.

16. The composition of claim 14 wherein one or both polymer segments B and C are hydrophobic.

17. The composition of claim 16 wherein at least one of polymer segments B and C can crystallize.

18. The composition of claim 11 wherein said hydrophobic block segment can crystallize.

19. The composition of claim 11, wherein said hydrophobic block segment can crystallize and is a gradient copolymer.

20. A process for producing a composition comprising a functional agent, and the tailored polymer of claim 1 bound to said functional agent wherein said tailored polymer is formed via nitroxide mediated controlled radical polymerization comprising:
   attaching an initiating alkoxyamine to said functional agent through a linking group to form a reactive agent,
   reacting said reactive agent with at least one ethylenically unsaturated monomer to produce a polymer segment;
   optionally, thereafter reacting said polymer segment with additionally at least one ethylenically unsaturated monomer to produce a block copolymer.

21. The process of claim 20 wherein said functional agent is bound to said tailored polymer in situ during processing.

* * * * *